United States Patent

Baker et al.

Patent Number: 5,120,661
Date of Patent: Jun. 9, 1992

[54] METHOD FOR DETECTION AND QUANTITATIVE ANALYSIS FOR WATER TREATMENT CHEMICALS

[75] Inventors: Gary L. Baker, Alexandria, Ky.; Ronald J. Christensen, Montgomery, Ohio

[73] Assignee: Diversey Corporation, Mississauga, Canada

[21] Appl. No.: 485,867

[22] Filed: Feb. 23, 1990

Related U.S. Application Data

[63] Continuation of Ser. No. 131,761, Dec. 11, 1987, abandoned.

[51] Int. Cl.⁵ .............................................. G01N 21/00
[52] U.S. Cl. ...................................... 436/164; 422/62; 73/61.41
[58] Field of Search ............... 436/10, 164, 3, 6, 56, 436/166, 172, 800; 422/62; 73/61.1 R; 210/745

[56] References Cited

U.S. PATENT DOCUMENTS

| | | |
|---|---|---|
| 2,815,328 | 12/1957 | Green et al. |
| 3,367,946 | 2/1968 | Stryker ............................ 436/3 X |
| 4,300,908 | 11/1981 | Kugel |
| 4,659,676 | 4/1987 | Rhyne, Jr. |
| 4,762,167 | 8/1988 | Dobson |
| 4,774,189 | 9/1988 | Schwartz ........................... 436/10 |
| 4,783,314 | 11/1988 | Hoots et al. ..................... 422/62 X |
| 4,894,346 | 1/1990 | Myers et al. .................... 436/129 X |
| 4,992,380 | 2/1991 | Moriarty et al. .................. 436/55 |

FOREIGN PATENT DOCUMENTS

| | | |
|---|---|---|
| 1019006 | 1/1953 | France |
| 2143638 | 2/1985 | United Kingdom |
| 2152937 | 8/1985 | United Kingdom |

OTHER PUBLICATIONS

Smart, P. L. "A Review of the Toxicity of Twelve Fluorescent Dyes used for Water Tracing." Chemical Abstracts, vol. 105, No. 18, 158339p (1984).
The Merck Index, 10th ed., New Jersey, Merck & Co., Inc., 1983, p. 595.
The NALCO Water Handbook, New York, McGraw-Hill Book Company, 1979, pp. 38-8 to 38-13.

Primary Examiner—Robert J. Warden
Assistant Examiner—Jeffrey R. Snay
Attorney, Agent, or Firm—Wood, Herron & Evans

[57] ABSTRACT

An inert water soluble dye is added to a concentrated water treatment composition. This mixture is added to the water in a circulating water system such as a cooling tower. The concentration of the dye and the concentration of the actives in the treatment composition are proportionate to each other. The concentration of the treatment composition in the water system can be determined by measuring the percentage of light absorbed by the dye in the water. This can be determined by use of a colorimeter. Fluorescein is the preferred dye.

7 Claims, 1 Drawing Sheet

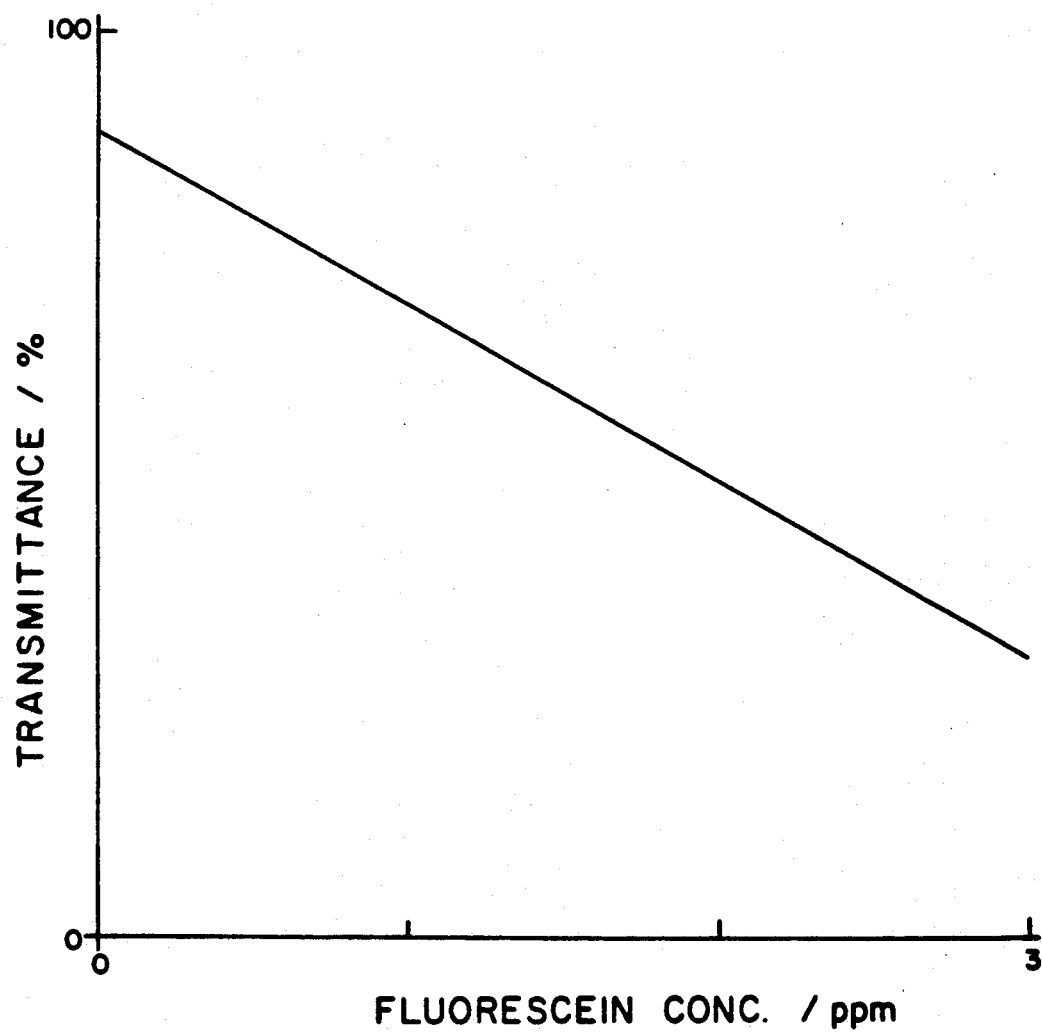

METHOD FOR DETECTION AND QUANTITATIVE ANALYSIS FOR WATER TREATMENT CHEMICALS

This application is a continuation of application Ser. No. 131,761, filed Dec. 11, 1987, now abandoned.

BACKGROUND OF THE INVENTION

There are many different types of circulating water systems. Three basic types are water cooling towers which are open systems, boilers which are closed systems, and chilled water systems which are also closed. More recently, cross-over cooling water systems, where both the tower water and the chilled water are combined for a period, are being employed.

If ultrahigh purity water were available in ample supply there would be little reason to chemically treat any of the water added to these systems. In actuality, however, highly pure water is rarely available. Therefore, operators of water systems must resort to chemical treatment to prevent damage to the water system which can be caused by the impurities contained in water.

There are literally dozens of treatment compositions that are currently added to these systems. The selection of the particular treatment agent depends on the type of water added, the particular water system employed, and operational conditions. Some of the types of treatment compositions added include dispersants, descalants, scale inhibitors, algacides, biocides, corrosion inhibitors, oxygen scavengers and pH modifiers. In each category of composition there are also a number of different particular compositions which can be used to accomplish the desired result. For example, phosphonates are typically used as anti-scaling agents and corrosion inhibitors. Chelating agents such as ethylenediamine tetraacetic acid and nitrilotriacetic acid are also anti-scaling agents. Corrosion inhibitors also include aromatic azoles, alkaline earth metal molybdates and so on.

Water systems are treated by adding the selected desired treatment agents separately or more likely a combination of treatment agents is dispensed into the water in the water system. Combinations for example could include corrosion inhibitors in combination with descalants and biocides for a water cooling tower. A boiler treatment composition may for example include an anti-scalant, corrosion inhibitors and oxygen scavenger.

Whether the treatment compositions are added separately or as a mixture it is necessary to determine the concentration level of the treatment agent or agents in the water system. Typically this has been done by simply taking a sample of the water in the system and performing a series of chemical analysis such as pH and various titrations to determine the concentration of the chemicals added.

One chemical that has been added in the past has been tannins and a similar composition lignins. These are anionic compositions which have been used in the past as dispersants. They are no longer the preferred dispersants since certain water soluble polymers have been developed which by far surpass the dispersing activities of these chemicals. However, these chemicals did have one incidental advantage in that they had a color and could be visually detected within a water system. Thus the boiler operator could visually detect the concentration of tannin or lignin in the system. When used they were added separately to the system. Therefore they did not provide any indication of the concentration of any other component.

Because tannins and lignins are anionic they cannot be added to a mixture which includes cationic treatment agents such as other dispersants and the like which can be cationic. In concentrated solutions, the tannins and lignins would precipitate out of solution and be totally ineffective.

Accordingly, to determine the concentration of the treatment agents in a water system one must perform complex titrations and other tests. This is inefficient and can result in ineffective treatment or a waste of treatment agents.

SUMMARY OF THE INVENTION

The present invention is premised on the realization that a inert water soluble dye can be added and mixed with a concentrated treatment agent for a water system and be dispensed into the water system with the treatment agent. Since the amount of dye added to the water system is proportional to the amount of treatment agent added, the concentration of the treatment agent can be determined by measuring the concentration of the dye. Thus, the intensity of the color of the water provides an indication of the concentration of the treatment agent.

The present invention is further premised on the realization that the concentration of the treatment agent can then be detected by photometric and/or visual means and more specifically by a colorimetric method using visible light detectors. Fluorometric techniques may also be used. Selecting a dye with an absorbance which varies linearly with concentration at application concentration simplifies colorimetric analysis.

A photodegradable dye can be employed which when dispensed into the environment does not have a long lasting and noticeable effect on the environment and thus is environmentally acceptable. Surprisingly even in open systems such as water cooling towers where the water treatment agent is exposed to sunlight for a period of time a photodegradable dye can be employed without being totally inactivated when exposed to the light.

The advantages of the present invention will be further appreciated in light of the following detailed description and drawing in which:

BRIEF DESCRIPTION OF THE DRAWING

The FIGURE is a graphical depiction of the percent transmittance of 500 nm light relative to the concentration of a fluorescein dye.

DETAILED DESCRIPTION OF THE INVENTION

The present invention is a method of detecting the concentration of a water treatment composition in a water circulating system. The water treatment composition is a water based concentrated composition which incorporates a known quantity of a water soluble dye as well as a known quantity of one or more water treating chemicals. By detecting the concentration of the dye in a circulating water system one can also detect the corresponding concentration of the active ingredients of the water treatment composition or determine the amount of treatment product added. Also, when slug doses of the treatment is initially added, system water volume can be determined.

For purposes of the present invention, a water circulating system includes water cooling towers, evaporative condensers, boilers, and chilled water systems. Each of these systems require one or more treating chemicals or agents added to the water in the systems. Treatment compositions for the present invention basically includes any chemical which will be added to the water of a water cooling tower, boiler or chilled water system to alter any physical or chemical activity of the water. These chemical compositions include dispersants including organophosphorous compounds particularly organophosphorous carboxylic acids and the phosphonates. Typically the phosphonates include aminomethylene phosphonic acid and 1-hydroxylethyladene-1,1-diphosphonic acid. A commonly employed organic phosphorus carboxylic acid is 2-phosphonobutane-1,2,4-tricarboxylic acid.

These chemical compositions also include corrosion inhibitors such as alkaline earth metal molybdates, chromates and nitrite salts which are used at higher concentrations. Sodium molybdate is an anodic inhibitor and is the most commonly used molybdate inhibitor. Other corrosion inhibitors include aromatic azoles primarily used as corrosion inhibitors for copper and its alloys. Generally included within the aromatic azoles are benzotriazole, tolyltriazole and mercaptobenzothiazole.

Biocides are also employed. These may include $ClO_2$, chlorine, chlorine release compounds such as chlorinated isocyanurates, hypochlorites, and chlorinated hydantoins. Oxidizers such as chlorine, present in the cooling water system at concentrations greater than about 0.5 ppm, will degrade the fluorescein. Hydrogen peroxide tends to cause precipitation of the fluorescein when added to the treated cooling water. Quaternary ammonium compounds are the primarily non-oxidizing biocides and biostats. These are cationic surface active chemicals which are most effective against algae and bacteria at alkaline pH.

Chelants are also used as hardness sequestering agents. These include ethylenediaminetetraacetic acid (EDTA) and nitrilotriacetic acid (NTA).

Anionic polymers are widely used in industrial boilers for sludge conditioning. These are credited with inhibiting scale formation and with removing existing scale by several mechanisms. Such anionic polymers include polyacrylates, polymethacrylates, polymaleic anhydride and various copolymers of these. Synthetic sulfonated polymers, synthetic carboxylated polymers and carboxymethylcellulose are also used.

Oxygen scavengers are used primarily in boiler operations and chilled water systems. Oxygen scavengers include sodium sulfite, hydrazine and erythorbic acid and salts thereof. In boilers neutralizing amines are used to combat the interaction of carbon dioxide with steam which forms carbonic acid. The neutralizing amines may include cyclohexylamine, morpholine, and diethylaminoethanol. Filming amines are used to establish a continuous protective film over surfaces in the after boiler section. These would include octadecylamine.

There are also a variety of different chemicals used to adjust boiler water pH including sodium hydroxide and sodium carbonate. Other compositions may include sodium nitrate which inhibits caustic embrittlement, and anti-foaming agents like polyglycols, silicones and polyamides.

One or more of these chemical compositions or agents are added to a water system in an attempt to attain a desired use concentration generally defined in parts per million of the actives of the chemical compositions. These are however purchased and dispensed as concentrated aqueous solutions which are generally defined in terms of grams of actives per liter of concentrated treatment composition. Where the treatment composition is a mixture of treatment agents the concentration of each agent is proportioned to the desired use concentration.

Thus a known concentration $Q_1$ of an inert water soluble dye is added to the concentrated treatment composition. For use in the present invention the water soluble dye must be inert. For purposes of the present invention, inert means that it must have neither appreciable anionic nor cationic characteristics in concentrated forms. It must also be thermally stable, and stable to both reducing and slightly oxidizing environments.

The dye must be photodetectable to provide advantageous benefits of the present invention. By photodetectable it must be detected by light reflectance, transmittance or absorbance in the ultraviolet, infrared, or visible spectrums. Preferably, the dye will be fluorescent and detectable by one of these means using visible light. Under these circumstances the concentration can be initially visually detected and can subsequently be detected by means of a colorimeter which is quite inexpensive relative to ultraviolet and infrared spectrophotometers. Visual detection can be facilitated by the use of a color comparator.

Further, since most water systems periodically bleed off water in the system and dispense this into the environment, the dye should be nonstaining and non-persistent. More particularly it should be a dye which degrades naturally and quickly in the environment and preferably would be a photodegradable dye. Suitable non-persistent dyes include fluorescein, Rhodamine B, Rhodamine WT and Lissamine. All of these are non-persistent and are currently used in water flow studies in the environment. A preferred dye is fluorescein which degrades very quickly in the environment.

The dye will be added to the concentrated treatment composition and dispensed with the treatment composition into the water system. The amount of dye added to the concentrated treatment composition will depend on the amount of treatment composition intended to be added to the water system to provide the desired concentration level of the treatment composition generally in terms of parts per million. It is preferable that the concentration of the dye present in the water system will be within a concentration range where the change in amount of dye will provide a linear response on the spectrophotometer. This is shown with respect to fluorescein in the FIGURE.

This FIGURE shows the percent transmittance of light at 500 nm versus the concentration of fluorescein at a concentration level of 0.3-3 parts per million. At this concentration range the change in concentration of fluorescein with respect to transmittance is basically linear making it very easy to determine photometrically the concentration of fluorescein in the water system.

Since the concentration of the fluorescein in the treatment agent is known and the concentration of the fluorescein in the water can be detected, the concentration of the water treatment agent can be determined. The optimum concentration of fluorescein is 1.2 ppm. Thus, where the desired concentration of treatment composition is 120 ppm, the treatment composition should be 1% fluorescein.

This of course will change depending on the dye used, the wave length of light at which this is measured and the optimum concentration of the particular dye.

The invention will be further appreciated in light of the following examples of concentrations of components that could be added to boilers, water cooling towers and chilled water systems. These provide typical desired optimum concentrations and typical desired concentrations of the fluorescein dye that would be added to these compositions.

| Cooling Water Treatment Formula | | |
|---|---|---|
| Order of Addition | Ingredient | Percent |
| 1 | Water | 87.6 |
| 2 | Phosphonate (HEDP - 60%) | 3.0 |
| 3 | Polyacrylic Acid - 50% | 1.0 |
| 5 | Tolyltriazole - 50% | 2.0 |
| 6 | Fluorescein | 0.4 |
| 4 | Sodium Hydroxide - 50% | 6.0 |
| Applied at 300-600 ppm conc. in the system. | | |

| Boiler Water Treatment Formula | |
|---|---|
| Ingredient | Percent |
| Water | 72.35 |
| Disodium Phosphate | 6.00 |
| Polyacrylic Acid - 50% | 1.50 |
| Sodium Sulfite | 5.00 |
| Potassium Hydroxide | 15.00 |
| Fluorescein | 0.15 |
| Maintained at 800 to 1200 ppm in the boiler. | |

These compositions are added merely by way of example and the particular chemical compositions that would be added or combinations of chemical compositions that would be added to the particular system will vary widely particularly depending on the make-up water added to the system which varies based on geographic location.

In carefully conducted field tests where a water treatment composition having 0.4% fluorescein was added to a water cooling tower, the accuracy of this method was compared to a standard industry test, the thorium nitrate test. By measuring make up water and the mass of treatment composition added, the concentration was determined to be 384 ppm. Using a colorimeter to detect the concentration of fluorescein, the concentration was measured at 341 ppm. Using color comparator, the concentration was determined to be 400 ppm. The thorium nitrate test, which tests for phosphonate concentration, indicated the concentration was 469 ppm. Thus, detecting concentration by detecting fluorescein concentration is substantially more accurate than the thorium nitrate test and much simpler to apply.

The proceeding has been a detailed description of the present invention. This has been exemplary in nature and is intended to describe how to practice the invention as well as the best mode of practicing the invention. However, as is obvious from the specification this can be modified by various changes in treatment compositions, dyes and detection techniques.

Thus, the present invention should be limited only by the following claims in which we claim:

1. A method of detecting a concentration treatment composition present in a cooling tower said cooling tower having water and said treatment composition comprising:
    adding a mixture into said water present in said cooling tower, said mixture comprising an inert photodegradable water soluble dye and said treatment composition in a defined proportion such that the concentration of the treatment composition remains in direct proportion to the concentration of said dye in the cooling tower, detecting the concentration of said treatment composition present in said water by colorimetric detection of the concentration of said inert photodegradable water soluble dye in said cooling tower.

2. The method claimed in claim 1 wherein said dye is selected from the group consisting of water soluble fluorescein, Rhodamine B, Rhodamine WT and Lissamine.

3. The method claimed in claim 2 wherein said dye is water soluble fluorescein, maintained at concentration levels between 0.3 and 3.0 ppm in said water.

4. The method claimed in claim 1 wherein the concentration of said dye is visually detected.

5. A method of detecting a concentration of a treatment composition present in an open water system, said open water system having water and said treatment composition said method comprising:
    adding a mixture into said water present in said open water system, said mixture comprising a known amount of a photodegradable inert water soluble dye and a known amount of said treatment composition, said dye being selected from the group consisting of water soluble fluorescein, Rhodamine B, Rhodamine WT or Lissamine,
    detecting the concentration of said treatment composition in said water by colorimetric detection of the concentration of said due in said system.

6. The method claimed in claim 5 wherein said photodegradable inert water soluble dye comprises fluorescein.

7. The method claimed in claim 6 wherein said water system is selected from the group consisting of cooling towers, chilled water systems and boilers.

* * * * *

UNITED STATES PATENT AND TRADEMARK OFFICE
CERTIFICATE OF CORRECTION

PATENT NO. :  5,120,661

DATED : June 9, 1992

INVENTOR(S) : Gary L. Baker and Ronald J. Christensen

It is certified that error appears in the above-identified patent and that said Letters Patent is hereby corrected as shown below:

Column 6, line 38, after "said water," insert a --,--.

Column 6, line 47, delete "due" and insert in place thereof --dye--.

Signed and Sealed this

Nineteenth Day of October, 1993

Attest:

BRUCE LEHMAN

Attesting Officer

Commissioner of Patents and Trademarks